(12) United States Patent
Yakhno et al.

(10) Patent No.: US 6,874,357 B2
(45) Date of Patent: Apr. 5, 2005

(54) METHOD FOR STUDYING LIQUID AND DEVICE FOR CARRYING OUT SAID METHOD

(76) Inventors: Tatjana Anatoljevna Yakhno, ul. Lopatina, 9-123, Nizhny Novgorod, 603163 (RU); Vladimir Grigorievich Yakhno, ul. Lopatina, 9-123, Nizhny Novgorod 603163 (RU); Ivan Ivanovich Shmeljov, ul Suslovoi, 7-32, Nizhny Novgorod 603109 (RU); Anatoly Gennadievich Sanin, ul. Suetinskaya, 2-42, Nizhny Novgorod 603035 (RU); Evgeny Valerievich Krotov, ul Chaadaevn, 16-6, Nizhny Novgorod, 603163 (RU); Yuri Yakovievich Brodsky, ul. Usilova, 2-151, Nizhny Novgorod, 603163 (RU)

( * ) Notice: Subject to any disclaimer, the term of this patent is extended or adjusted under 35 U.S.C. 154(b) by 63 days.

(21) Appl. No.: 10/466,845
(22) PCT Filed: Aug. 1, 2002
(86) PCT No.: PCT/RU02/00016
  § 371 (c)(1),
  (2), (4) Date: Jul. 21, 2003
(87) PCT Pub. No.: WO02/059595
  PCT Pub. Date: Aug. 1, 2002
(65) Prior Publication Data
  US 2004/0216515 A1 Nov. 4, 2004
(30) Foreign Application Priority Data
  Jan. 23, 2001 (RU) .......................................... 2001101946
(51) Int. Cl.[7] .............................................. G01N 29/00
(52) U.S. Cl. .................... 73/64.53; 73/53.04; 73/61.73; 73/574
(58) Field of Search .............................. 73/64.53, 54.07, 73/61.73, 61.74, 54.24, 24.01, 335.03, 335.06, 574

(56) References Cited

U.S. PATENT DOCUMENTS 4,320,659 A * 3/1982 Lynnworth et al. ........... 73/589

(Continued)

OTHER PUBLICATIONS

Ultrasonic detection of porous medium characteristics, Peterson, Jr. et al. Nov. 27, 2003, US 2003/0217599 A1.*

(Continued)

Primary Examiner—Hezron Williams
Assistant Examiner—Jacques M. saint-Surin
(74) Attorney, Agent, or Firm—John D. Gugliotta

(57) ABSTRACT

The present invention relates to physical chemistry and can be used for a quality test of liquids, in particular, multi-component liquid products, to ascertain the conformity of various process liquids, pharmaceutical preparations, foodstuffs, biological liquids to standard in pharmacology, food processing and chemical industries, and in medical diagnostics. The method of invention enables determining the mechanical impedance within a drop (1) of test liquid having a specified volume, in the preferred embodiment, 5 mcl, placed on the surface of a piezoelectric resonator (3) of ultrasound frequencies, which provides for excitation of shear modes within drop (1) while it is drying up. The obtained time dependence of the mechanical impedance of drop (1) is used as the information parameter. This information parameter is rather sensitive to the state of the liquid-crystalline structure of multi-component liquids, therefore, comparing the obtained time dependence with the same data for the etalon specimen allows one to assess the composition of a multi-component liquid, test the quality of liquid products, for example, foodstuffs, assess the prospective effectiveness of medical treatment with various medical preparations through analysis of a biological liquid, etc.

In the apparatus of invention, the mechanical impedance of test liquid is determined from the disbalance voltage of a bridge circuit (9) comprising a piezoelectric resonator of ultrasound frequencies (3), in preferred embodiments, from the amplitude and/or phase of the disbalance voltage, which ensures high accuracy of measurements.

26 Claims, 4 Drawing Sheets

U.S. PATENT DOCUMENTS

| | | | |
|---|---|---|---|
| 5,118,464 A | * 6/1992 | Richardson et al. | 376/252 |
| 5,187,980 A | * 2/1993 | Blair et al. | 73/599 |
| 5,460,046 A | * 10/1995 | Maltby et al. | 73/623 |
| 5,533,402 A | 7/1996 | Sarvazyan et al. | 73/645 |
| 5,659,129 A | 8/1997 | Asoyan et al. | 73/54.25 |
| 5,804,698 A | 9/1998 | Belonenko et al. | 73/1.83 |
| 5,836,200 A | 11/1998 | Belonenko et al. | 73/61.79 |
| 6,047,602 A | * 4/2000 | Lynnworth | 73/632 |

OTHER PUBLICATIONS

Apparatus and method for analyzing a liquid in a capillary tube of a hematology instrument, Apr. 8, 2004, US 2003/0065143 A1.*

* cited by examiner

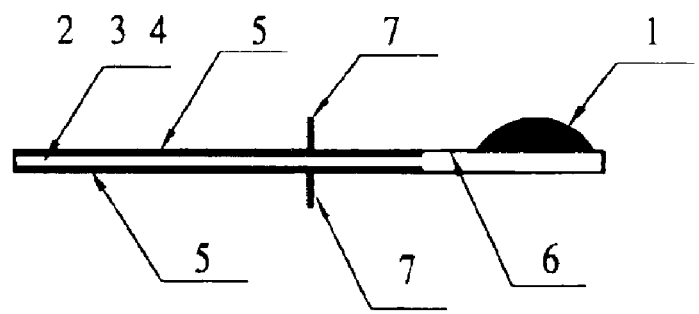
Fig. 1?
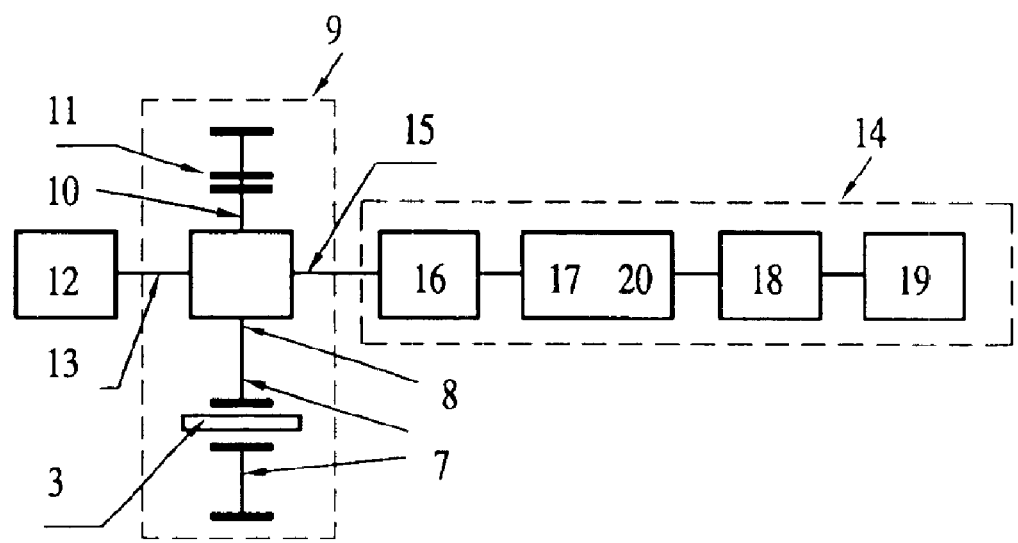
Fig. 2?

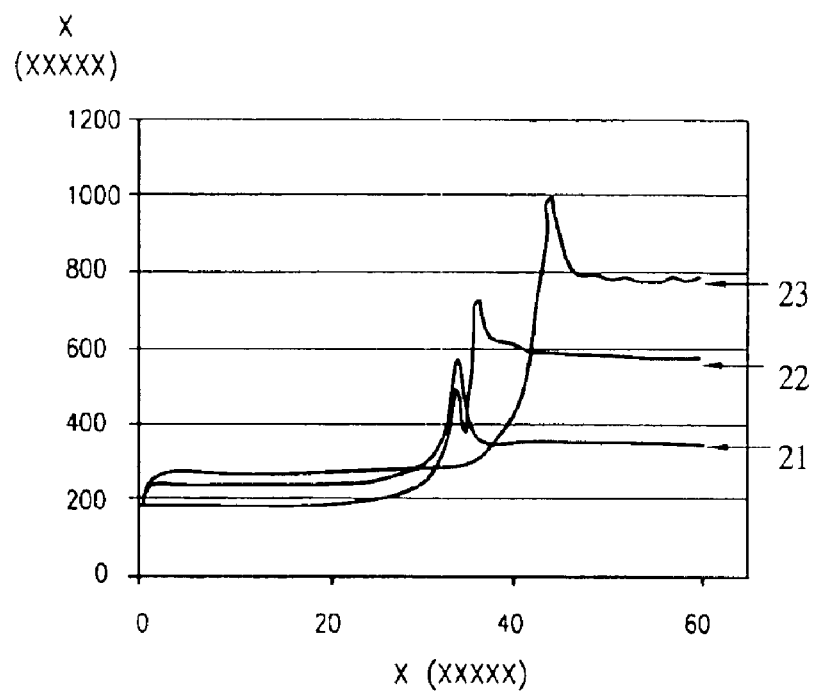
*Fig. 3?*
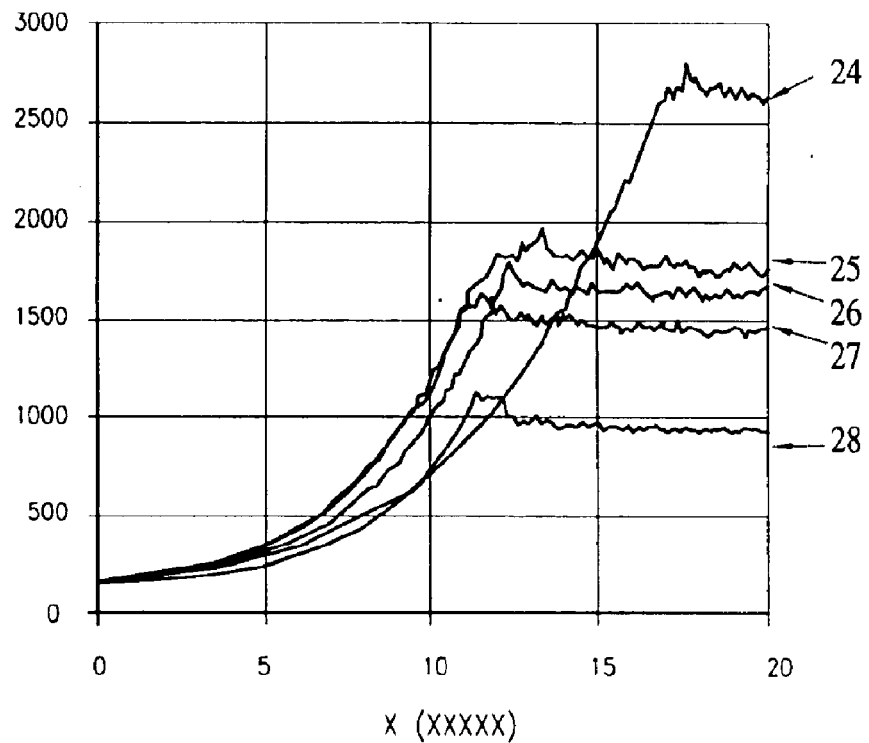
*Fig. 4?*

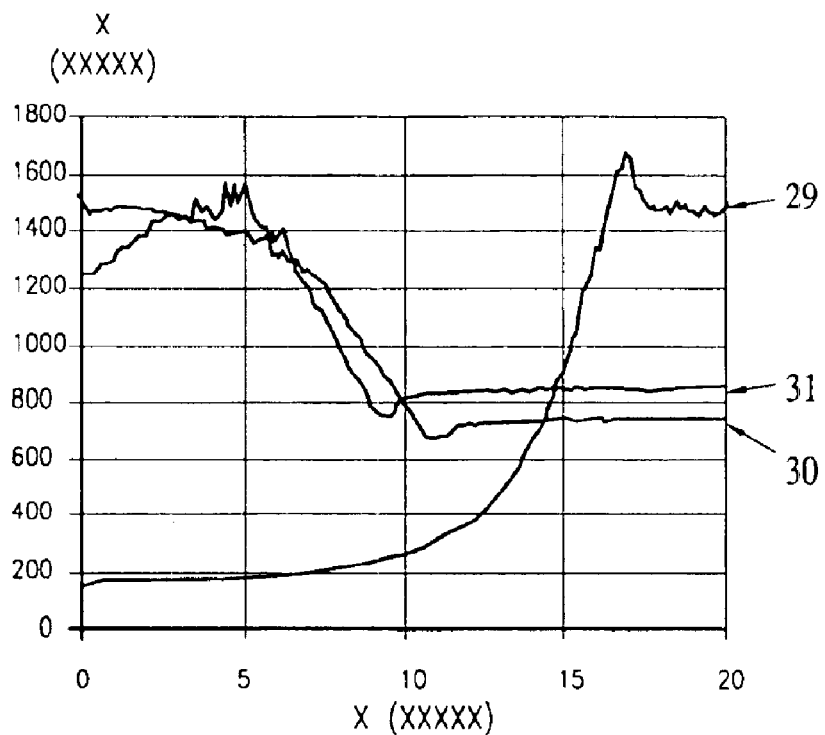
Fig. 5?
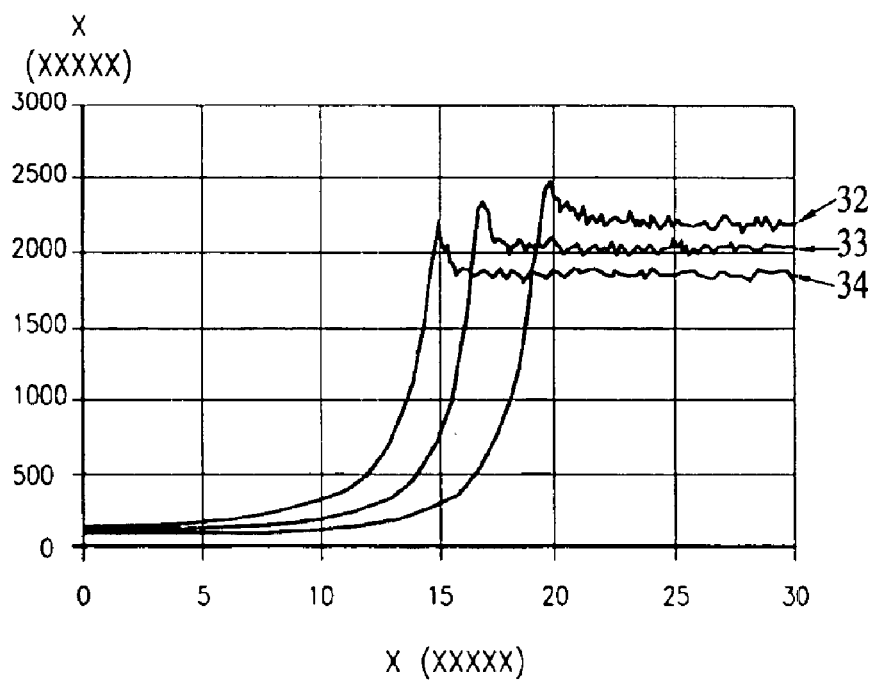
Fig. 6?

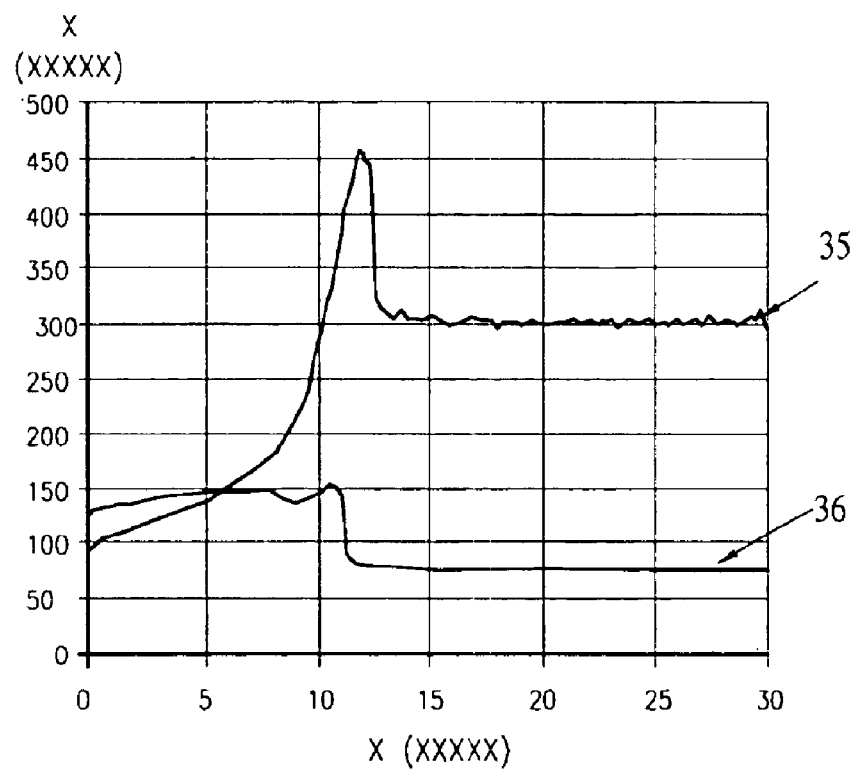
Fig. 7?
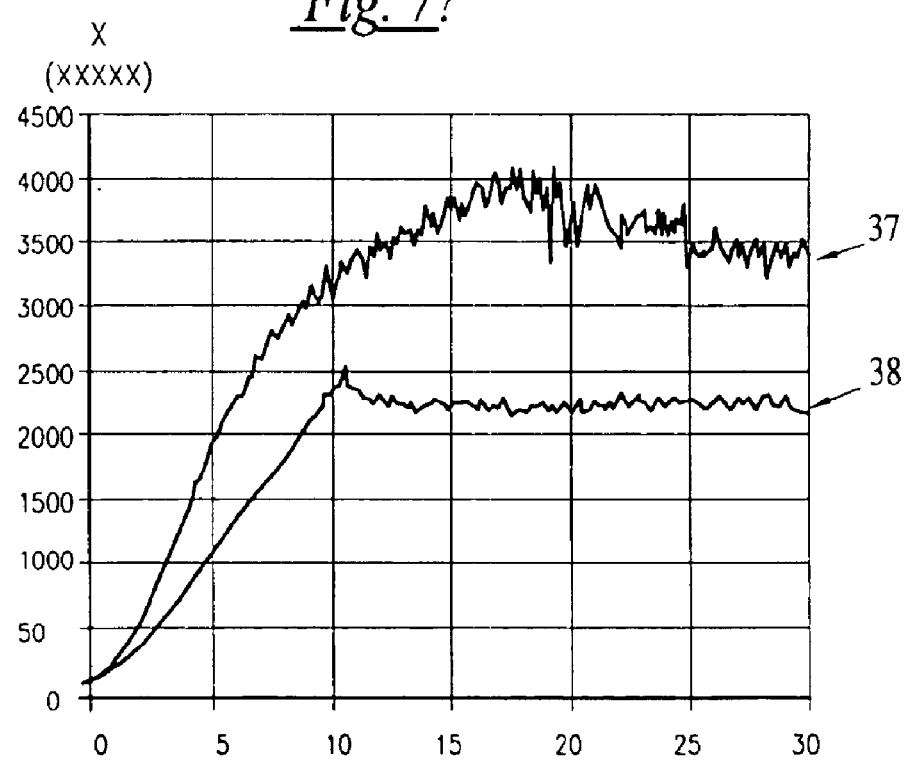
Fig. 8?

METHOD FOR STUDYING LIQUID AND DEVICE FOR CARRYING OUT SAID METHOD

FIELD OF TECHNOLOGY

The present invention relates to physical chemistry and can be used for a quality test of liquids, in particular, multi-component liquid products, to ascertain the conformity of various process liquids, pharmaceutical preparations, foodstuffs, biological liquids to standard in pharmacology, food processing and chemical industries, and in medical diagnostics.

BACKGROUND OF THE INVENTION

RF U.S. Pat. No. 2,137,126 describes a method for investigating of biological liquids, which involves IR-spectrum analyser assisted study of the liquid previously diluted with a water-alcohol mixture in a 1:1 proportion. The major drawback of this method is that it causes deterioration of the native structure of the biological liquid, which carries essential information on its nature.

There is a description of the effect of dehydration self-organization of biological liquids (V. N. Shabalin, S. N. Shatokhina, Autogeneous rhythms and self-organization of biological liquids//BEBM, 1996, vol. 122, No. 10, p. 364–371). This effect consists in a characteristic redistribution of the components in a drop of a multi-component biological liquid as it is drying up, which causes the resulting dry film to have a distinct zone structure and a certain super-molecular formations reflecting the peculiarity of its liquid-crystalline structure governed by chemical composition.

This principle underlies, for example, the method for assessing the homeostasis state of a living organism, as described in RF U.S. Pat. No. 2,007,716. Essentially, it is a morphological study on a dried-up drop of biological liquid in polarized light and assessment of the normal and pathological structures formed thereby.

The same principle is used in the method for assessing the homeostasis state of a living organism according to RF U.S. Pat. No. 2,127,430. In this method a liquid biological medium, for example, blood plasma or serum, urine, tear drop, etc., dries up under the impact of some external or internal factors, and when the water has evaporated, the resulting crystallogram is examined in nonpolarized light. If the structural elements are clustered and complex morphological formations take place, development of a pathological process and disturbance of the homeostasis are presented; in contrast, well-ordered and oriented elements in the absence of large complex aggregations indicate improvement of the physical condition, hence, the homeostasis is judged as compensated.

The shortcoming of this technique, just as of the above method described in RF U.S. Pat. No. 2,007,716, is a long time the specimen take to dry up (24 to 48 hours) and, therefore, a long duration of the research. It also takes specially trained personnel to do proper diagnostics of morphological structures.

U.S. Pat. No. 5,798,452 describes a method for liquids analysis, which involves immersing a piezoelectric resonator in the liquid in question, this resonator being an element of an ultrasonic generator and coming in the form of a thin plate providing for excitation in it of thickness shear modes. The piezoelectric plate is designed to ensure confinement of a thin film of the liquid within the assigned area on its surface. The shear modes excited in the piezoelectric plate induce similar oscillations in the confined layer of the test liquid. This causes a shift of frequency of the ultrasonic generator through the electrical impedance arising thereof which, in turn, is determined by the mechanical impedance of the test liquid layer being confined on the surface of the piezoelectric plate. By measuring the frequency shift of said ultrasonic generator one can find the mechanical impedance of said confined layer of the liquid, which provides data on the viscosity and density of said liquid. In accordance with the invention described in the same patent, apparatus is provided for liquid analysis using this method. The apparatus includes an ultrasonic frequency oscillator incorporating a piezoelectric resonator, frequency meter and recorder. The test liquid comes in direct contact with the resonator surface.

The method and apparatus for investigating a liquid as described in U.S. Pat. No. 5,798,452 enable one to determine viscosity and density of the test liquid at a specified point in time. However, this parameter does not provide sufficient information on the composition of a liquid if it is multi-component.

DETAILED DESCRIPTION OF THE INVENTION

The present invention is directed to a method and apparatus providing fast and efficient analysis of a liquid and enabling characterization of composition of a multi-component liquid.

In accordance with the invention, in the same way as in the method described in U.S. Pat. No. 5,798,452, a certain volume of a test liquid is set on a hard substrate in specified environment, and shear modes in the ultrasound frequency range are excited within said volume of the test liquid in order to determine the mechanical impedance of said volume of the test liquid.

In contrast to the prior art, according to the present invention, an assigned volume of test liquid in the form of a drop is placed onto said substrate, said drop is further subject to drying, and the mechanical impedance is determined at set instants of time during the drop drying up process with the time dependence of the mechanical impedance obtained during the drying-up of said drop being recorded, said dependence being used as the information parameter.

In a particular embodiment of the invention said drop of the test liquid dries up in a natural way.

In another embodiment said drop is subject to forced drying.

It is advisable to compare the obtained results with those achieved in the study of etalon sample in order to identify deviations of the information parameter from the same parameter of etalon sample.

In another embodiment the test liquid is a solution of inorganic matter.

In still another embodiment the test liquid is a solution of organic matter.

In a different embodiment the test liquid is a solution of inorganic materials mix.

In a further embodiment the test liquid is a solution of organic materials mix.

In a still further variation of the invention the test liquid is a solution of organic and inorganic materials mix.

In a particular embodiment of this variation the test liquid is a medical preparation.

In another embodiment of this variation of the invention the test liquid is a soft drink.

In still another embodiment of this variation the test liquid is an alcoholic drink.

In a different variation of the invention the test liquid is a liquid fuel.

In a further variation the test liquid is a biological liquid.

In one embodiment of this variation the test liquid is a biological liquid of plants.

In another embodiment of this variation the test liquid is a biological liquid of animal origin.

In a further variation of the invention said hard substrate is an element of the resonator.

In a still further variation said mechanical impedance is determined from the disbalance voltage of a bridge circuit comprising said resonator.

In a particular embodiment of this variation the mechanical impedance is determined by measuring the amplitude of the disbalance voltage of said bridge circuit.

In another embodiment of this variation the mechanical impedance is determined by measuring the phase of the disbalance voltage of said bridge circuit.

It is essential that said drop of test liquid be fully dried.

The apparatus of the invention for analyzing a multi-component liquid, same as the device described in U.S. Pat. No. 5,798,452, comprises an ultrasonic generator, a resonator that includes as an element a hard substrate coming in contact with the test liquid, and a recorder.

In contrast to the prior art liquid analyzers, in accordance with the present invention the ultrasonic generator is designed as master oscillator, the resonator being included in one arm of the bridge circuit, the other arm of said bridge circuit incorporating a [? capacitor], the master oscillator being connected to one diagonal of said bridge circuit, the recorder being connected to the other diagonal of said bridge circuit and being designed as a means for measuring at least one parameter of the bridge circuit disbalance voltage.

In a particular variation of the invention the recorder includes a means for measuring the amplitude of said bridge circuit disbalance voltage.

In another variation the recorder includes a means for measuring the phase of said bridge circuit disbalance voltage.

It is advisable that the resonator be made piezoelectric.

In one embodiment of the invention a quartz resonator is used.

SUMMARY OF THE INVENTION

In accordance with the invention, a method is provided for determining the mechanical impedance of a test liquid drop having a specified volume, in one embodiment, 5 mcl, set on the surface of a piezoelectric resonator of ultrasound frequencies, which is designed with a provision for excitation in said drop of shear modes during the drying-up of this drop. The time dependence of the mechanical impedance of the drop, obtained thereof is used as the information parameter. Such information parameter is rather sensitive to the state of the liquid-crystalline structure of multi-component liquids, therefore, comparing the obtained time dependence with the same data for the etalon specimen allows one to assess the composition of a multi-component liquid, test the quality of liquid products, for example, foodstuffs, assess the prospective effectiveness of medical treatment with various medical preparations through analysis of a biological liquid, etc.

The apparatus of the invention provides for determining the mechanical impedance, based on the disbalance voltage of a bridge circuit comprising said piezoelectric resonator of ultrasound frequencies, in different embodiments using the amplitude and/or phase of the disbalance voltage, which ensures a high accuracy of measurements.

BRIEF DESCRIPTION OF THE DRAWINGS

The essence of the invention will be better understood by referring to the detailed description below and the drawings, in which:

FIG. 1 is a sensing element of the apparatus of the invention for analyzing liquids.

FIG. 2 is a circuit design of the apparatus providing for analyzing liquids in the method of the invention.

FIG. 3 illustrates time dependences of the modulus values for the mechanical impedance of a drop of salt solution, obtained during the drying-up of this drop and reduced to the viscosity values.

FIG. 4 illustrates time dependences of the modulus values of the mechanical impedance for a drop of beer and for a drop of beer diluted with tap water, which were obtained during the drying-up of either drop and reduced to viscosity values.

FIG. 5 shows time dependences of the modulus values of the mechanical impedance for a drop of wine, a drop of wine diluted with water, and a drop of wine diluted with ethanol, obtained during the drying-up of either drop and reduced to viscosity values.

FIG. 6 illustrates time dependences of the modulus values of the mechanical impedance for a drop of healthy human urine and a drop of urine mixed with albumin in various concentrations, which were obtained throughout the drying of each drop and reduced to viscosity values.

FIG. 7 is illustrating time dependences of the modulus values of the mechanical impedance for a drop of saliva from a healthy man and a drop of saliva from a virus hepatitis patient, which were obtained during drying-up of the respective drops and reduced to viscosity values.

FIG. 8 shows time dependences of the modulus values of the mechanical impedance for the drops of blood serum from a [burnt] patient, analyzed before and after subjecting the patient to [extracorporal heparincryoprecipitation] treatment, which were obtained during drying-up of the respective drops and reduced to viscosity values.

DESCRIPTION OF THE PREFERRED EMBODIMENT

According to the method of the invention for studying a liquid with the apparatus as shown in FIG. 2 comprising the sensor as shown in FIG. 1, Drop 1 (FIG. 1) of a test liquid of specified volume, for example, 5 mcl, is placed on a hard substrate 2 in given conditions, i.e., at set values of temperature, pressure and humidity. In the preferred embodiment of the invention, substrate 2 is an element of a resonator 3 which should be piezoelectric, for example, a quartz one. Resonator 3 in this embodiment is a thin quartz plate 4 with the length largely in excess of the width and height of said plate. Electrodes 5 are deposited on the wide top and bottom surfaces of quartz plate 4. In [the preferred embodiment ?] quartz plate 4 includes a part 6 having its top and bottom surfaces free of electrodes 5. It is advisable to place drop 1 of the test liquid onto part 6 of the quartz plate, i.e., hard substrate 2. Electrodes 5 are linked to [connectors, conductors] 7 which connect resonator 3 in one arm 8 of a bridge circuit 9 (FIG. 2), the other arm 10 of said bridge circuit incorporating a [compensating] capacitor 11. The capacitance of [compensating] capacitor 11 is equal to that formed by electrodes 5 of resonator 3.

Master oscillator 12 connected to one diagonal 13 of bridge circuit 9 which in a particular embodiment may be made symmetric, generates sinusoidal [voltage] oscillations of ultrasound frequency. This voltage creates an electric field between electrodes 5 of resonator 3, which excites in piezoelectric plate 4 that functions as hard substrate 2 compression-extension vibrations in the direction perpendicular to the direction of said electric field. These vibrations excite shear modes in drop 1 placed on substrate 2. The presence of drop 1 on the surface of resonator 3 causes a change in the electrical conductivity of resonator 3, said change being determined by the mechanical impedance of the test liquid. Variation of the electrical conductivity of resonator 3 brings about a corresponding change in the disbalance voltage of bridge circuit 9. Specific parameters of bridge circuit 9 and the operating frequency of resonator 3 are governed by the type of a piezoelectric used and are chosen such that the disbalance voltage is proportional to the mechanical impedance of the test liquid drop, in particular, the disbalance voltage amplitude is inversely proportional to the modulus of the mechanical impedance of this drop, whereas the disbalance voltage phase is proportional to the phase of the mechanical impedance of said drop. The disbalance voltage is recorded by recorder 14 which is connected to the other diagonal 15 of bridge circuit 9 and comes as a means for measuring at least one parameter of the disbalance voltage of the bridge circuit.

In one embodiment recorder 14 is designed as a means for measuring the amplitude of the bridge circuit disbalance voltage. In this case the disbalance voltage is amplified by amplifier 16, detected by amplitude detector 17, integrated by integrator 18 and through an analog-digital converter (ADC) 19 entered into the computer (not shown on the drawing).

In another embodiment recorder 14 may come as a means for measuring the phase of the bridge circuit disbalance voltage. In this case, phase detector 20 is used in recorder 14 instead of amplitude detector 17.

To upgrade the measurements accuracy, in still another embodiment recorder 14 may come as a means for simultaneous measuring of both amplitude and phase of the bridge circuit disbalance voltage (not shown on the drawing).

Next, drop 1 either dries up in a natural way or is subject to forced drying (if necessary, until the test liquid has dried up completely), and the mechanical impedance of said drop is measured at set instants of time throughout the process of drying of the drop, in accordance with the procedure described above. The time dependence of the mechanical impedance of the test liquid drop is also recorded during the drying-up of said drop and used as the information parameter FIGS. 3–8 illustrate time dependences of the mechanical impedance modulus values for drops of different test liquids, reduced to the viscosity values of these liquids, taken in arbitrary units.

FIG. 3 illustrates time dependences of the modulus values for the mechanical impedance of a 5 mcl drop, reduced to the values of viscosity η (in arbitrary units), taken throughout the drying-up of a drop of salt solution under investigation: curve 21 shows a corresponding dependence for a 0.9% solution of NaCl (physiological solution); curve 22 is the dependence for a drop of solution A, obtained directly after dissolving in said physiological solution of a certain amount of crystalline NaCl; curve 23 shows the dependence obtained for a drop of the same solution A 24 hours after dissolving in said solution of crystalline NaCl. Comparing the time dependences 21–23 reveals a two-phase [character] of the liquid-crystalline structure of the solution immediately after dissolving in it of crystalline salt, and setting of a new [uniform; unified] structure in 24-hours' time.

FIG. 4 illustrates time dependences of the modulus values for the mechanical impedance of a 5-mcl drop of beer "Toistyak" before and after thinning the beer with tap water. The time dependences were taken throughout the drying-up of the respective drops and reduced to the values of viscosity η (in arbitrary units): curve 24 is a corresponding dependence for the 100% quality product, curves 25–28 show the corresponding dependences for the beer diluted with water in a 4:1, 3:1, 2:1 and 1:1 proportion, respectively. Curves 24–28 reveal considerable differences in the time dependences of the quality and the water-diluted product, according to a degree of dilution.

FIG. 5 shows time dependences of the modulus values for the mechanical impedance of a 5 mcl drop of dry red wine "Kollektsia Masterov" ("Masters' Collection") before and after diluting said wine with tap water, which were obtained during the drying-up of the respective drops and reduced to viscosity η (the values are taken in arbitrary units): curve 29 is a corresponding dependence for the natural 100% quality product; curves 30, 31 illustrate, respectively, similar dependences for said wine thinned in a 4:1 proportion with water and ethanol, which were taken immediately after dilution. Curves 29–31 demonstrate essential differences in the time dependences for the quality-, water-diluted, and the ethanol-diluted wine.

Curves 32–34 in FIG. 6 illustrate time dependences of the modulus values for the mechanical impedance of a 5 mcl drop of healthy urine (curve 32) and a similar drop of urine mixed with dry albumin in various concentrations (curves 33,34), obtained throughout the drying of the respective drops and reduced to the values of viscosity η (in arbitrary units); curve 34 corresponds to a double content of albumin as compared to curve 33. The curves expose the differences in the evaporation dynamics of the drops of urine under study.

FIG. 7 shows time dependences of the mechanical impedance modulus for a 5 mcl drop of saliva from a healthy man (curve 36) and a man infected with virus hepatitis B (curve 35); the time dependences were obtained during the drying-up of said drops and reduced to viscosity values, η (in arbitrary units).

It is obvious that curves 35 and 36 are largely different.

Curves 37, 38 in FIG. 8 illustrate time dependences of the mechanical impedance modulus values corresponding to various instances in the drying-up of a 5 mcl drop of blood serum from a [burnt] patient (curve 37) and a similar drop of blood serum from a patient exposed to extracorporal heparincryoprecipitation treatment (curve 38), which are reduced to the viscosity values, η (taken in arbitrary units). Curves 37, 38 reveal a change in the blood serum composition during the treatment.

The above examples provide sufficient evidence that the present invention enables fast and effective analysis of a variety of liquids including multi-component liquid products.

Commercial Value

The present invention can be used for a [?] quality test of liquids, in particular, multi-component liquid products, to ascertain the conformity of various process liquids, pharmaceutical preparations, foodstuffs, biological liquids to standard in pharmacology, food processing and chemical industries, and in medical diagnostics.

It is worth noting that the invention does not require expensive equipment and highly skilled personnel to be realized and that standard components and means can be used.

What is claimed is:

1. A method for investigating a liquid in which a certain volume of test liquid at specified conditions is put on a hard substrate, shear oscillations in the ultrasonic range are excited within said volume and the mechanical impedance therein is determined, wherein the volume of test liquid is preset and arranged as a drop on said substrate, said drop being subject to drying, while the mechanical impedance being determined at specified instants of time during the process of drying of said drop and the time dependence of said mechanical impedance being recorded all through this process, said time dependence being used as the information parameter.

2. The method according to claim 1 wherein said drop of test liquid dries up in a natural way.

3. The method according to claim 1 wherein said drop of test liquid is subject to forced drying.

4. The method of claim 1 or 2 or 3 wherein the obtained results are compared with the data achieved in study of etalon sample to reveal deviations of the information parameter from that of the etalon sample.

5. The method of claim 1 or 2 or 3 or 4 wherein the test liquid is a solution of inorganic matter.

6. The method of claim 1 or 2 or 3 or 4 wherein the test liquid is a solution of organic matter.

7. The method according to claims 1 to 4 wherein the test liquid is a solution of any one of inorganic materials mix.

8. The method according to claims 1 to 4 wherein the test liquid is a solution of any one of organic materials mix.

9. The method according to claims 1 to 4 wherein the test liquid is a mixed solution of any one of organic and inorganic materials.

10. The method according to claim 9 wherein the test liquid is a medical preparation.

11. The method according to claim 9 wherein the test liquid is a soft drink.

12. The method of claim 9 wherein the test liquid is an alcoholic drink.

13. The method of claim 1 or 2 or 3 or 4 wherein the test liquid is liquid fuel.

14. The method of claim 1 or 2 or 3 or 4 wherein the test liquid is a biological liquid.

15. The method of claim 14 wherein the test liquid is a bioliquid from plants.

16. The method of claim 14 wherein the test liquid is a bioliquid of animal origin.

17. The method of claims 1 to any one of 14 wherein said hard substrate is an element of the resonator.

18. The method according to claims 1 to any one of 15 wherein said mechanical impedance is determined from the disbalance voltage of a bridge circuit comprising said resonator.

19. The method according to claim 18 wherein the mechanical impedance is determined by measuring the amplitude of the disbalance voltage of said bridge circuit.

20. The method according to claim 18 or 19 wherein the mechanical impedance is determined by measuring the phase of the disbalance voltage of said bridge circuit.

21. The method according to claims 1 to 20 wherein said drop of test liquid is subject to any one of drying until fully dried.

22. Apparatus for analyzing a multi-component liquid, comprising an ultrasonic generator, a resonator including as a component a hard substrate coming in contact with the test liquid, and a recorder, wherein the ultrasonic generator is designed as master oscillator, said resonator being incorporated in one arm of the bridge circuit, the other arm of said bridge circuit incorporating a [compensating] capacitor, said master oscillator being connected to one diagonal of said bridge circuit and the recorder being connected to the other diagonal of the bridge circuit, said recorder being a means for measuring at least one parameter of the disbalance voltage of said bridge circuit.

23. Apparatus according to claim 22 wherein the recorder comprises a means for measuring the amplitude of the disbalance voltage of the bridge circuit.

24. Apparatus according to claim 22 or 23 wherein the recorder includes a means for measuring the phase of the disbalance voltage of the bridge circuit.

25. Apparatus according to claim 22 or 23 or 24 wherein the resonator is made of a piezoelectric material.

26. Apparatus according to claim 25 wherein the resonator is made of quartz.

* * * * *